(12) United States Patent
Moore et al.

(10) Patent No.: US 7,644,637 B2
(45) Date of Patent: Jan. 12, 2010

(54) METHOD AND APPARATUS FOR TRANSFER OF SAMPLES IN A CONTROLLED ENVIRONMENT

(75) Inventors: Thomas M. Moore, Dallas, TX (US); Gonzalo Amador, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 315 days.

(21) Appl. No.: 11/860,663

(22) Filed: Sep. 25, 2007

(65) Prior Publication Data
US 2009/0078060 A1      Mar. 26, 2009

Related U.S. Application Data

(60) Provisional application No. 60/846,978, filed on Sep. 25, 2006.

(51) Int. Cl.
*G01N 1/00* (2006.01)
(52) U.S. Cl. ..................................... 73/863
(58) Field of Classification Search .............. 73/863, 73/864.21, 864.31, 864.35; 250/440.11–42.11
See application file for complete search history.

(56) References Cited

U.S. PATENT DOCUMENTS

| | | | | |
|---|---|---|---|---|
| 3,958,124 A | 5/1976 | Koch et al. | ............. | 250/442.11 |
| 4,272,682 A | 6/1981 | Swann | ................... | 250/442.11 |
| 4,672,797 A | 6/1987 | Hagler | ....................... | 53/467 |
| 4,703,181 A | 10/1987 | Swann et al. | ........... | 250/442.11 |
| 4,797,261 A | 1/1989 | Swann et al. | ................ | 422/102 |
| 4,833,330 A | 5/1989 | Swann et al. | ............. | 250/443.1 |
| 4,950,901 A | 8/1990 | Jones et al. | ............... | 250/443.1 |
| 4,996,433 A | 2/1991 | Jones et al. | ............... | 250/443.1 |
| 5,131,797 A | 7/1992 | Christiansen et al. | ....... | 414/219 |
| 5,472,566 A | 12/1995 | Swann et al. | ........... | 204/192.34 |
| 5,753,924 A | 5/1998 | Swann | ..................... | 250/443.1 |
| 6,205,870 B1 * | 3/2001 | Hosokawa et al. | ......... | 73/865.9 |
| 6,388,262 B1 | 5/2002 | Alani et al. | ............. | 250/442.11 |
| 6,410,925 B1 | 6/2002 | Armbruster et al. | .... | 250/442.11 |
| 6,538,254 B1 | 3/2003 | Tomimatsu et al. | .... | 250/442.11 |
| 6,576,910 B2 | 6/2003 | Hashikawa et al. | .... | 250/442.11 |
| 6,744,268 B2 | 6/2004 | Hollman | ..................... | 324/758 |
| 6,779,410 B2 * | 8/2004 | Koo et al. | ..................... | 73/863 |
| 6,927,400 B2 | 8/2005 | Rasmussen | ............ | 250/442.11 |
| 6,963,068 B2 | 11/2005 | Asselbergs et al. | .......... | 250/311 |
| 7,034,316 B2 | 4/2006 | Wagner et al. | ......... | 250/440.11 |
| 7,067,823 B2 | 6/2006 | Iwasaki et al. | ......... | 250/442.11 |
| 7,071,475 B2 | 7/2006 | Tomimatsu et al. | .... | 250/442.11 |
| 7,091,498 B2 | 8/2006 | Moriya | ................... | 250/442.11 |

(Continued)

*Primary Examiner*—Hezron Williams
*Assistant Examiner*—Tamiko D Bellamy
(74) *Attorney, Agent, or Firm*—John A. Thomas

(57) ABSTRACT

An apparatus for the transfer of samples from an analytical instrument has a sealable transfer capsule and a means for connecting the transfer capsule to a vacuum instrument, such as a FIB, through an interface connected to the instrument. The capsule has a door that can be opened to insert a sample holder, such as a TEM sample holder, into the instrument, and then closed when the sample holder holding an excised sample is retracted back into the transfer capsule. The instrument interface contains means for sealing the instrument before the transfer capsule holding a sample is disconnected, and for purging the transfer capsule with an inert gas. The sample may thus be transported in the sealed transfer capsule without exposure to the ambient atmosphere. The sample may be transported to and connected to a glove box also purged with an inert gas for examination or further operations.

25 Claims, 6 Drawing Sheets

U.S. PATENT DOCUMENTS

| | | | |
|---|---|---|---|
| 7,461,565 B2 * | 12/2008 | Pratt | 73/863 |
| 2006/0186336 A1 | 8/2006 | Giannuzzi et al. | 250/307 |
| 2006/0192116 A1 | 8/2006 | Baur et al. | 250/310 |

* cited by examiner

METHOD AND APPARATUS FOR TRANSFER OF SAMPLES IN A CONTROLLED ENVIRONMENT

CLAIM FOR PRIORITY

This application claims the priority of U.S. provisional patent application Ser. No. 60/846,978, filed Sep. 25, 2006.

BACKGROUND

There are a variety of situations in which microscopic samples excised from a bigger specimen require transfer under special conditions for further examination. Examples can be found in a variety of research fields, such as biotechnology, the semiconductor industry and other areas.

In the semiconductor industry and related areas, the in-situ lift-out method of TEM sample preparation in a focused ion-beam instrument (FIB) has become the method of choice for failure analysis during the last decade. During in-situ lift-out in the FIB, a tiny wedge is excised from the sample, attached to a grid for a transmission electron microscope (TEM), and transferred to the TEM for inspection. Depending on the particular specimen, these samples may require transfer in vacuum or in an inert atmosphere, such as argon.

There are systems in the art for the transfer of biological samples which require special conditions, for instance, samples taken from a frozen substance. However, some samples require not only temperature control, but react with the air and require transfer and handling in a controlled atmosphere such as an inert gas or other gas not reactive with or damaging to the sensitive sample.

There is a need for an integrated system for easy and secure transfer of TEM samples, or any other sensitive samples, to a final destination in an appropriate inert atmosphere. The system disclosed here is a low-cost solution for integrating the transfer process from the FIB to the TEM or any other analytical instrument.

DESCRIPTION

In the preferred embodiment, the transfer system comprises three major components: a sealed transfer capsule, a FIB interface assembly and an inert-atmosphere glove box.

The Sealed Transfer Capsule

Figure 1:
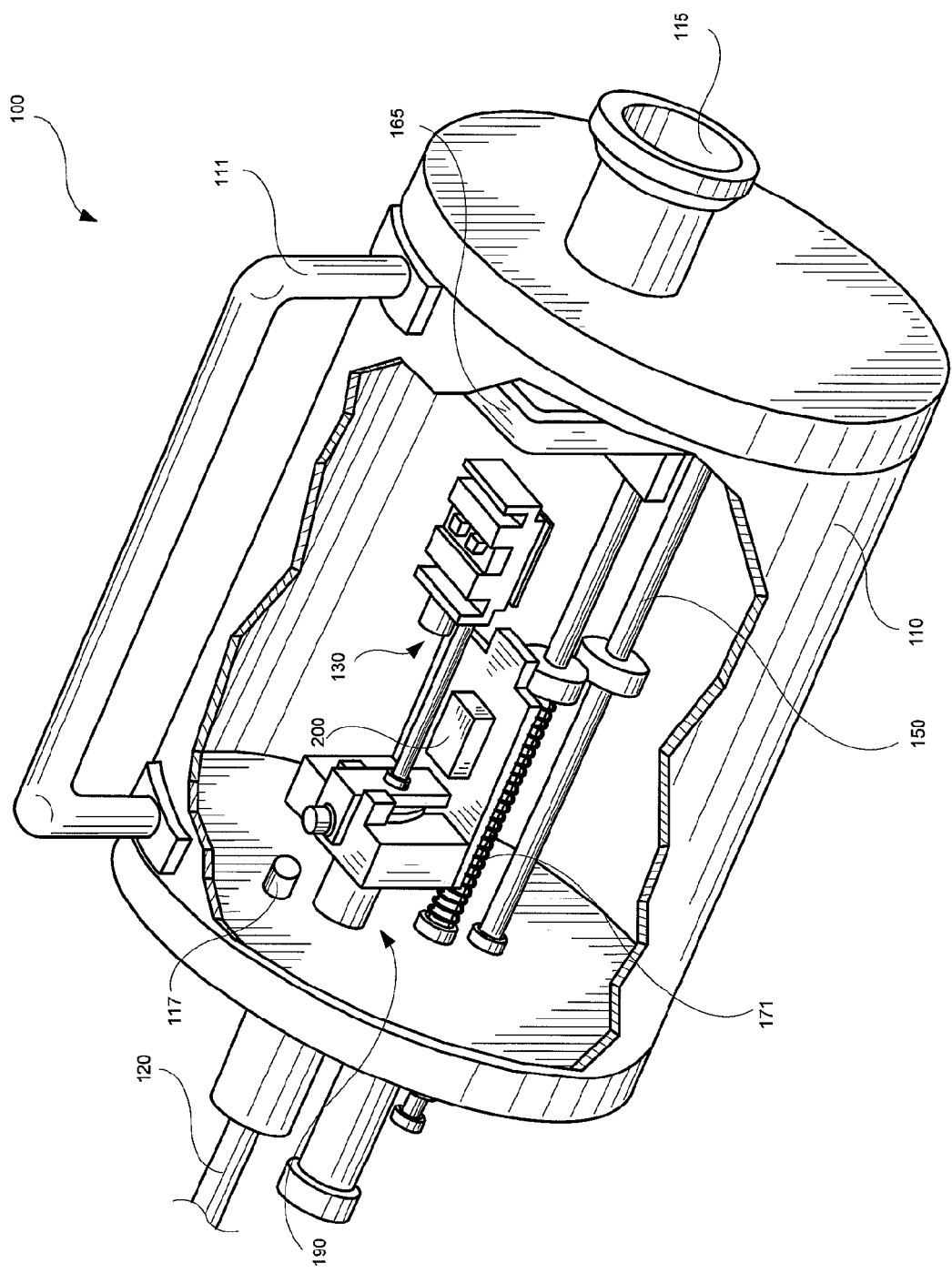
FIG. 1 is a perspective view of a sealed transfer capsule of the preferred embodiment.
Figure 2:
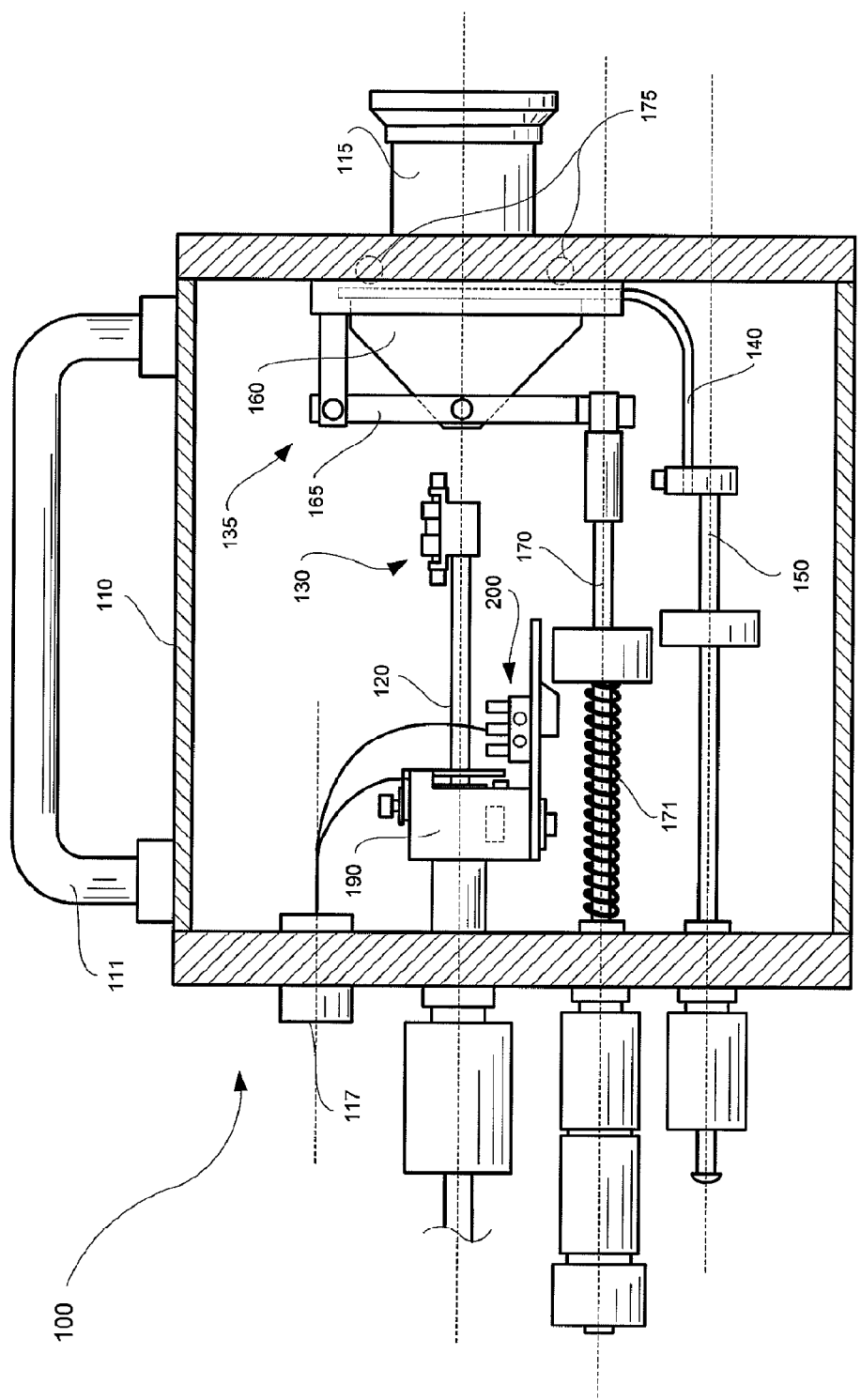
FIG. 2 is a sectional side view of a sealed transfer capsule with the capsule door closed.
Figure 3:
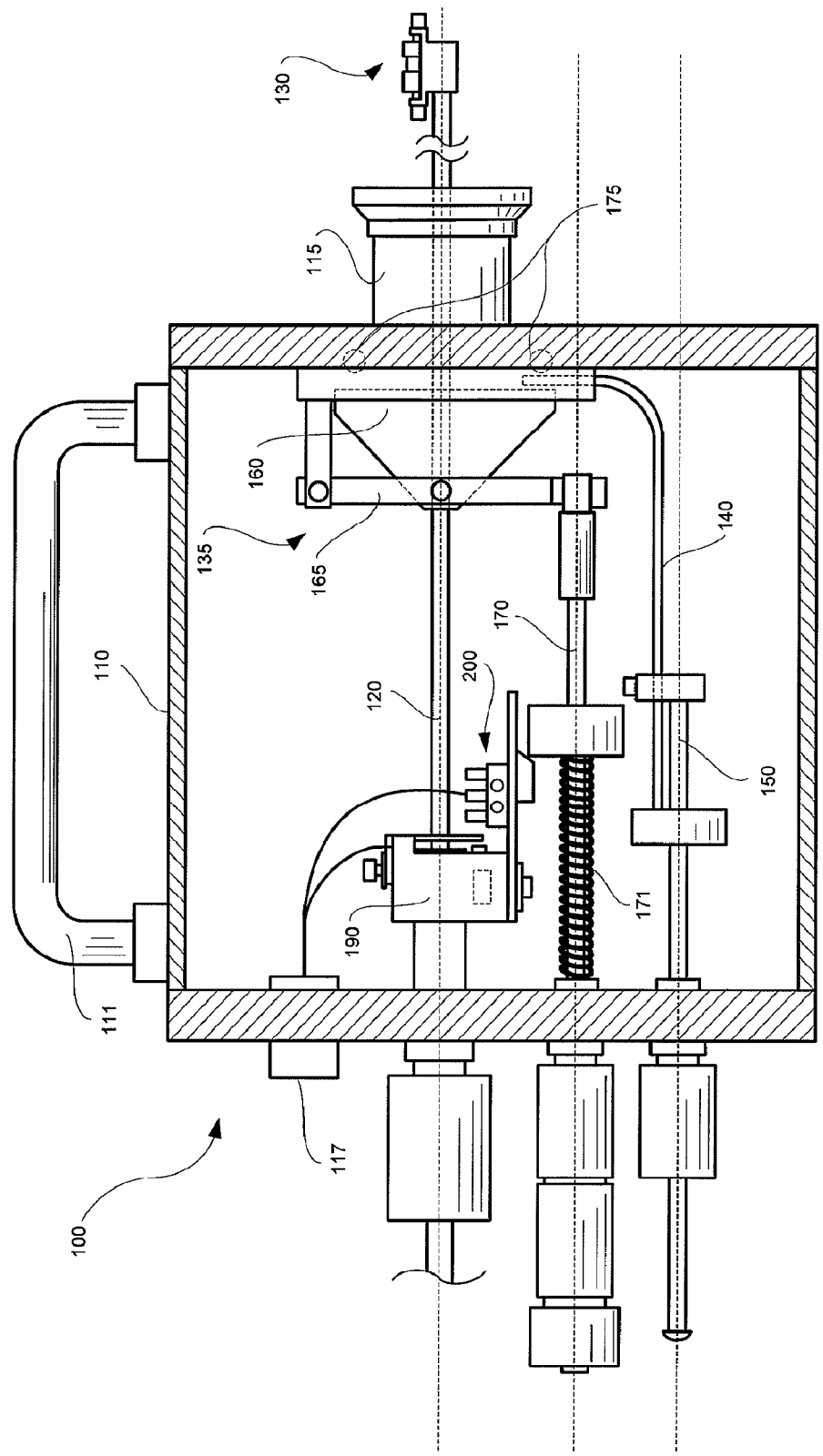
FIG. 3 is a sectional side view of a sealed transfer capsule with the capsule door open.

FIGS. 1, 2 and 3 depict the sealed transfer capsule (100) of the preferred embodiment. The transfer capsule (100) of the preferred embodiment comprises an airtight casing (110) with a capsule connecting flange (115) attached to it, a sample transfer rod (120), to which a removable sample holder (130) is attached, a capsule sensors bulkhead connector (117) and a capsule gate valve system (135). The airtight casing (110) has a handle (111) attached to it for convenient transportation and alignment. In this specification we refer to the sample holder as a "TEM sample holder," although the term will encompass sample holders for other types of instruments or samples.

The capsule gate valve system (135) comprises a means for closing and opening the capsule (100) to allow insertion and withdrawal of a sample holder (130). In the preferred embodiment, the means for opening and closing the capsule comprises a sliding capsule door (140), the door preferably formed from a flexible sheet and having an opened and a closed position. The capsule gate valve system (135) also has a capsule door clamp (160) attached to a capsule door clamp hanger (165), an O-ring seal (175), and a capsule door clamp rod (170) for moving the capsule door clamp hanger (165). The air-tight environment within the capsule is secured by clamping the sliding capsule door (140) against the O-ring seal (175). The capsule door clamp hanger (165) is attached to the capsule door clamp rod (170). The capsule door clamp rod (170) passes through a spring (171), which secures the clamp in operation. A clamp-status switch (200), preferably a microswitch, indicates the clamp status as clamped or un-clamped. (The sliding capsule door (140) was referred to as a "garage door" in the priority provisional application referenced above). Other means for opening and closing the capsule could be used, such as a pivoting door, a butterfly door, a door that swings out of the way of the capsule opening, or a door that is opened and moved out of the way via a cam and track. Unless otherwise specified, all such opening and closing means are generally referred to as a "door."

Figure 6:
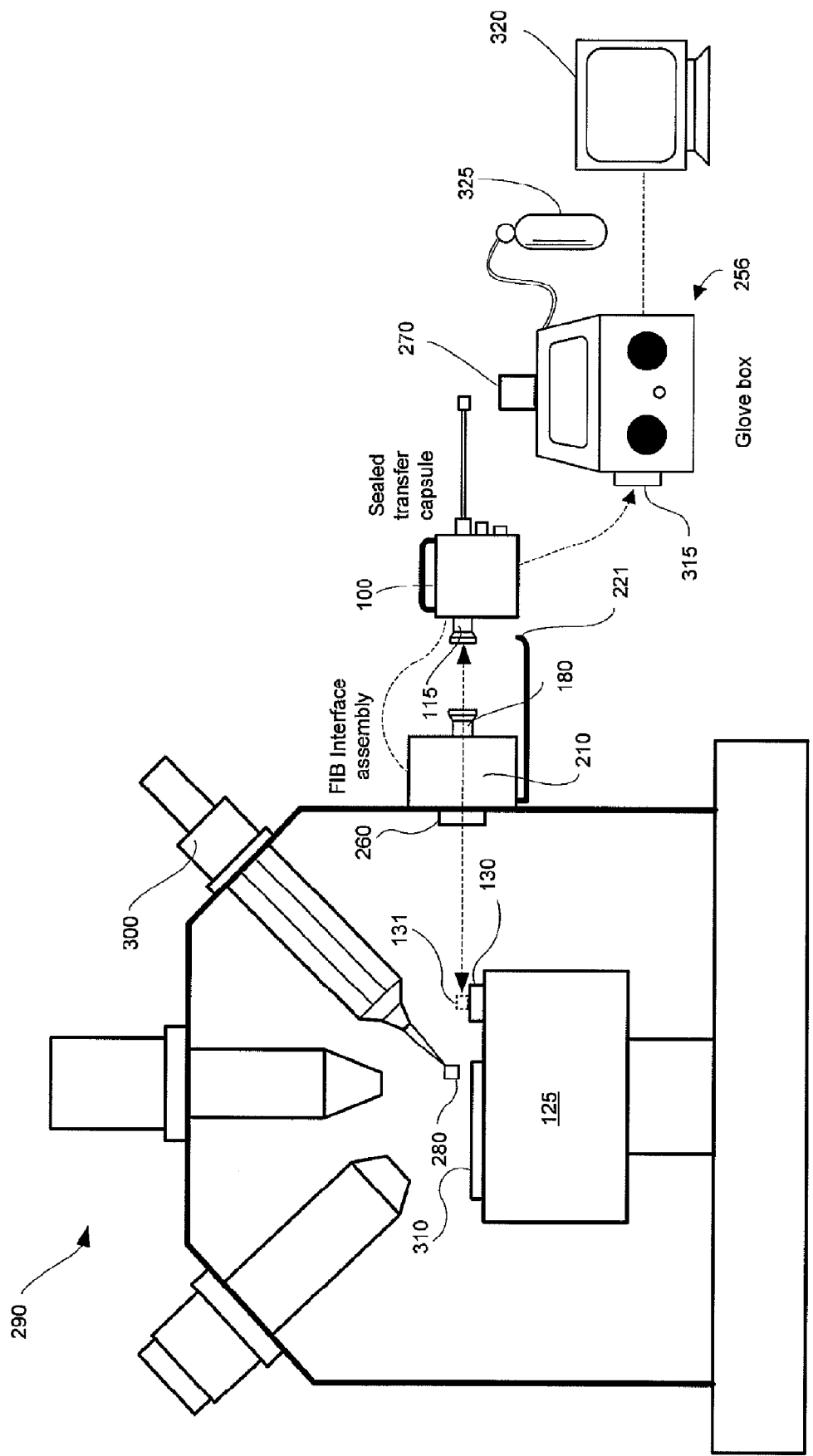
FIG. 6 is a schematic depiction of an embodiment of the transfer system in operation, using the example of a TEM sample transfer from a FIB.

The transfer capsule (100) is connected to the FIB interface assembly (210) as shown in FIG. 6, or to any other device where the specimen is located, using the capsule connecting flange (115).

The TEM sample holder (130), loaded with one or more empty TEM grids (131), is fastened to the end of the sample transfer rod (120). In this embodiment, a TEM sample holder (130) is used that has a dove-tail cross-section for sliding within a corresponding groove in the FIB or glove box sample stage. This kind of holder is known in the art. The dove-tail shape of the sample holder (130) is helpful to locate the sample holder on the FIB specimen stage (125). Other types of sample holders with different location means are known in the art and may be used. The sample transfer rod (120) can be moved forward to insert the TEM sample holder (130) into the FIB (290) and then retracted to remove the sample holder (130) from the FIB. A sample-retraction switch (190), preferably a microswitch, indicates when the TEM sample holder (130) is fully retracted into the capsule (100).

The Instrument Interface Assembly

Figure 4:
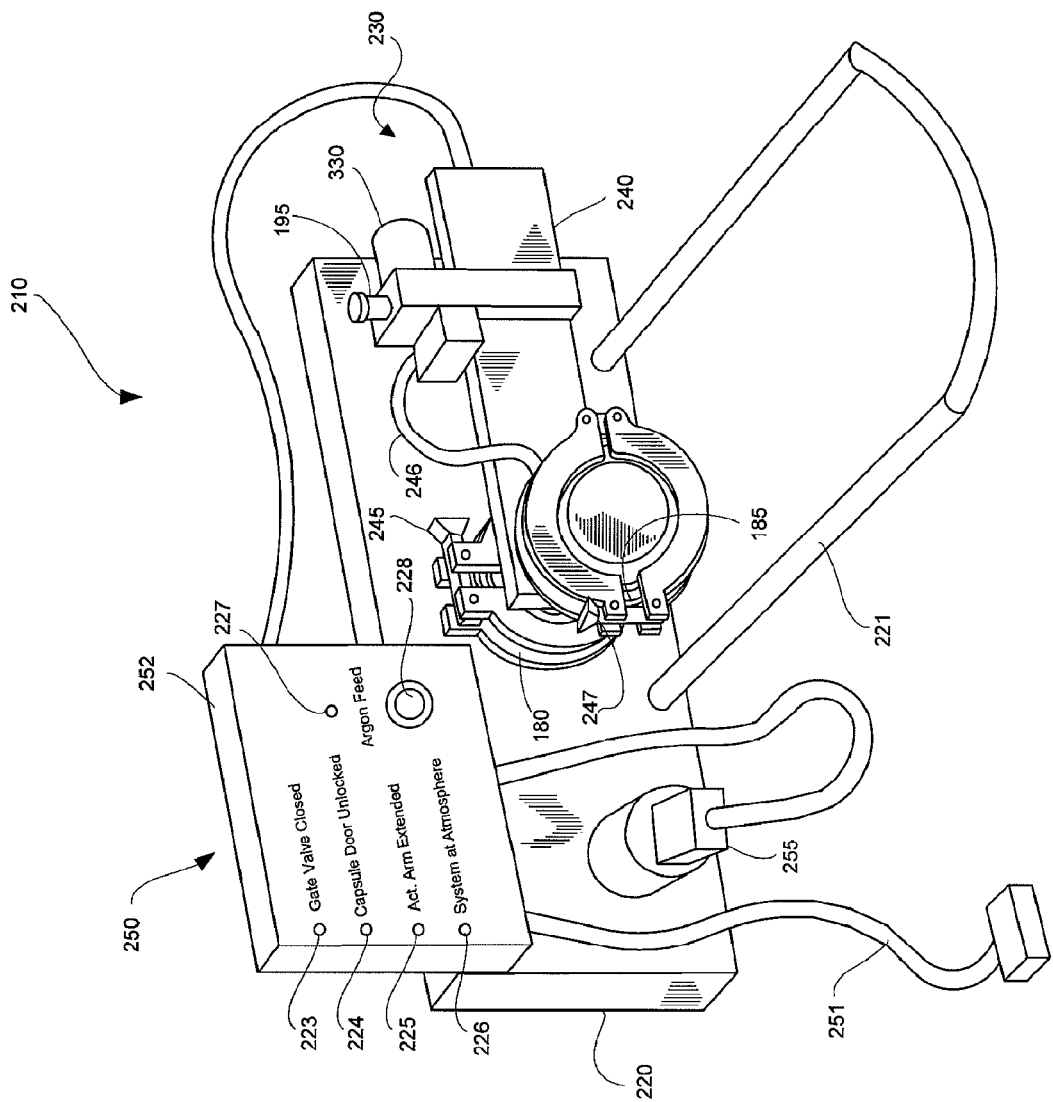
FIG. 4 is a perspective view of the FIB interface assembly for the preferred embodiment.

FIG. 4 shows the instrument interface assembly (210) of the preferred embodiment. Commonly, the instrument interfaced would be a FIB, although reference to such here should include any other vacuum instrument, such as a TEM or SEM. The FIB interface assembly (210) comprises docking hardware customized as appropriate for a particular model of FIB (290), a capsule purge system (230), a toggle-action automated gate valve (240) and vacuum interlock electronics (250), including the transfer capsule sensor cable (251). The docking hardware comprises the FIB interface plate (220), the FIB interface flange (180), the vacuum interlock electronics panel (252) and a support rest (221). The FIB interface assembly (210) mounts to a port (260) on the FIB (290) using the FIB interface plate (220) and an o-ring seal (not shown) integral with the FIB.

The outside face of the FIB interface assembly (210) has FIB interface flanges (180) and (185). These flanges (180) and (185) are also attached to the automated gate valve (240). The flange (185) matches the capsule connecting flange (115). The flange (180) is located between the automated gate valve (240) in FIG. 4 and the FIB interface plate (220). The automated gate valve (240) attaches to the FIB interface flange (180) using a first flange clamp (245) while the second flange (185) is available to mate with the capsule connecting flange (115) when the transfer capsule (100) is present, using a second flange clamp (247). The capsule purge system (230) comprises the automated gate valve (240) with the second flange clamp (247), a pipe or hose (246), through which argon or other media can be delivered, and a valve (330), typically a solenoid valve, for controlling the flow of argon or other media.

A suitable automated gate valve (240) is the model G1500-253-14, manufactured by Thermionics Vacuum Products of Port Townsend, Wash. Other valves could be used in different embodiments.

The vacuum interlock electronics assembly (250) monitors the operation of the system. The system status indicators (223-227), are preferably LED's and are placed on the cover of the vacuum interlock electronics panel (252), to provide a visual status of the several sub-systems.

The LED "Gate Valve Closed" (223) lights when the automated gate valve (240) is closed. When closed, the transfer capsule (100) internal volume is isolated from the FIB environment. This LED (223) is connected to a switch (195) on the automated gate valve (240).

The LED "Capsule Door Unlocked" (224) lights when the capsule door (140) is unlocked. This is sensed by the clamp-status switch (200) being closed by the capsule door clamp rod (170). (The status of the capsule door (140) being unlocked does not necessarily mean that it is open.) The clamp-status switch (200) energizes the "Capsule Door Unlocked" LED (224) in case the capsule door rod (150) is fully retracted.

The LED "Actuator Arm Extended" (225) lights when the sample transfer rod (120) is extended and no longer closes the sample-retraction switch (190). For this LED to light, the entire sample transfer rod (120) does not have to be extended to the FIB (290). In this embodiment, an extension of the sample transfer rod (120) of as little as 3 mm (⅛") from the fully retracted position will cause this LED (225) to light.

The LED "System at Atmosphere" (226) lights when the FIB vacuum level is near atmospheric pressure, around 0.1 torr or greater. A vacuum transducer (255) senses the pressure and actuates the "System at Atmosphere" LED (226). A conventional vacuum gauge (not shown), such as a Pirani gauge, may be used.

The LED "Argon Feed" (227) lights when the argon-feed pushbutton (228) is depressed and both the "Gate Valve Closed" (223) and "Capsule Door Unlocked" (224) LED's are lighted. If the "Argon Feed" pushbutton (228) is depressed and the "Argon Feed" LED (227) does not light, then no argon is being delivered into the transfer capsule (100). Gasses other than argon may be used, of course, depending on the application.

Figure 5:
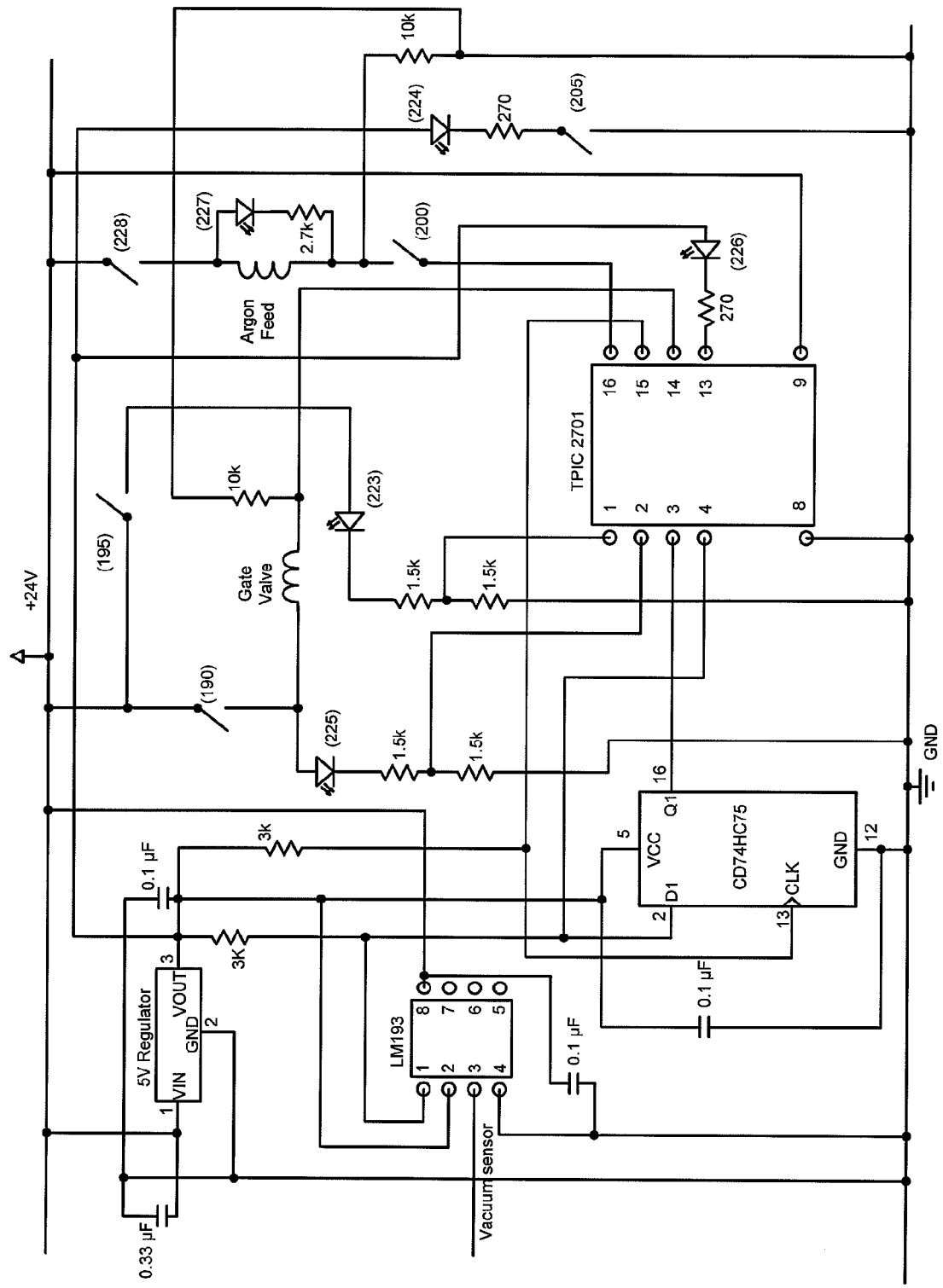
FIG. 5 is an exemplary schematic diagram of the electrical system of an embodiment of the transfer system.

FIG. 5 is a schematic of exemplary electrical wiring for the preferred embodiment. The integrated circuits shown in FIG. 5 include a common 5V voltage regulator, an LM193 dual comparator, a CD74HC75 quad bi-stable latch, and a TPIC2701 DMOS transistor array. All of these integrated circuits are available from Texas Instruments, Inc., and other suppliers. The reference numerals in parentheses in FIG. 5 correspond to those of the switches and indicators describe above. The reader should note that variations of the circuit depicted in FIG. 5 may be made by those skilled in the art to accomplish the same functions.

The Glove Box

The glove box (256) shown in FIG. 6 may be a modified industry-standard glove box similar to the type 100 manufactured by Terra Universal, Inc. of Fullerton, Calif. The glove box is modified to include a mount for a camera (270), a capsule support nest similar to the support rest (221) on the FIB interface assembly (210), and an interface flange matching the capsule connecting flange (115).

Method of Transfer of Samples in the Controlled Environment

The TEM sample (280) can be transferred in a controlled environment using the embodiment shown in FIG. 6. In FIG. 6, the sample is a TEM sample (280) excised from the specimen (310) using the nano-manipulator (300) and a FIB in-situ lift-out procedure, as is known in the art.

One or more empty TEM grids (131) can be loaded onto the TEM sample holder (130), which then can be fastened to the end of the sample transfer rod (120). To do so, the sliding capsule door (140) must be opened. The capsule door clamp (160) is first loosened, and then the capsule door rod (150) is pulled back until it hits a hard stop. Then the sample transfer rod (120) is extended and the TEM sample holder (130) is screwed on. After that, the sample transfer rod (120) is withdrawn back into the transfer capsule (100) and the capsule door (140) closed and locked.

Alternatively, if the FIB (290) is open to the atmosphere, the TEM sample holder (130) can be loaded directly onto the FIB specimen stage (125) by, for example, sliding the dove-tail base of the typical sample holder (130) into the corresponding dove-tail groove of a typical FIB specimen stage (125).

To introduce the TEM sample holder (130) via the sealed capsule, the procedure is as follows. The transfer capsule (100) is first placed onto the rods of the support rest (221). Then, the transfer capsule (100) is secured to the gate valve flange (185) using its gasket and the second flange clamp (247), followed by the transfer capsule sensor cable (251) attached to the capsule electronics bulkhead plug (117). During this procedure, the capsule handle (111) should be pointing straight up in the embodiment shown here because the face of the flanges (180, 185) are not concentric with the airtight casing (110) of the capsule (100).

Once the transfer capsule (100) is securely attached to the automated gate valve flange (185), the transfer capsule (100) must be opened to share the environment of the FIB (290). This can be achieved by opening the sliding capsule door (140) and the automated gate valve (240). As the reader can see from an inspection of the circuit shown in FIG. 5, the toggle-action automated gate valve (240) will be enabled to be opened when the sample-retraction switch (190) is closed, indicating the sample holder (130) is fully retracted into the capsule (100), the door clamp status switch is closed, indicating that the capsule door clamp (160) is loosened, and the vacuum sensor (255) signal indicates that the FIB vacuum is substantially at atmospheric pressure. To cause the automated gate valve (240) to open, the capsule door clamp (160) is loosened, and then the capsule door rod (150) is pulled back until it hits a hard stop. With the capsule door (140) open, the sample transfer rod (120) is extended towards the FIB (290), the action of which opens the gate valve (240). The FIB (290) is then pumped down to operating conditions. This will pump down the interior of the open transfer capsule (100) as well.

During pump-down of the FIB (290), the sample transfer rod (120) is inserted into the FIB (290) to dock the TEM sample holder (130) onto the FIB specimen stage (125), and then the sample transfer rod (120) is unscrewed from the TEM sample holder (130) and partially, but not entirely, retracted. Once specimen excision and lift-out procedures are completed and the TEM sample (280) or samples have been attached to the TEM grids (131), the sample transfer rod (120) is re-inserted into the FIB (290) to recapture the TEM sample holder (130) and retract it fully into the transfer capsule (100).

The vacuum interlock electronics (250) (see FIG. 5) senses the sample transfer rod's (120) fall retraction when the sample-retraction switch (190) is closed. When the sample-retraction switch (190) is closed and the vacuum sensor (255) signal goes low to indicate a vacuum in the FIB (290), the open automated gate valve (240) now closes, sealing and isolating the transfer capsule (100) from the FIB (290) environment. At this point a push-button control (228) can be activated to introduce an inert gas, such as argon, into the transfer capsule (100), if desired. After the introduction of the inert gas, the capsule door (140) is closed and locked, and the capsule door clamp (160) unloaded. The capsule gate valve system (135) seals the transfer capsule (100) and maintains the controlled environment at slightly above atmospheric pressure. Or, the sample may be transferred to another instrument in the sealed transfer capsule (100) while maintaining the vacuum as existing in the FIB (290).

The transfer capsule (100) is then detached from the FIB interface assembly (210) and preferably placed in a protective carrier (not shown) for transport to the glove box (256). The transfer capsule (100) should be properly oriented, with the handle (111) straight up in the embodiment shown. The transfer capsule (100) is next docked to the glove box (256) by connection to a mating flange (315) on the glove box (256). The glove box (256) may then be purged with the same inert gas as the transfer capsule (100). The means for purging the glove box may include a gas bottle (325) connected through a suitable valve (not shown) to the interior of the glove box (256). Within the protective atmosphere of the glove box (256), the TEM samples (280) attached to the TEM grids (131) can be transferred from the TEM sample holder (130) to any other sample holder. Using a video camera (270), attached to the glove box (256), an image of the TEM sample (280) can be viewed on the monitor screen (320). The TEM grid (131) with the TEM sample (280) attached to it can be transferred to any other TEM sample holder (such as that manufactured by Gatan, Inc. of Pleasanton, Calif.) using either tweezers (not shown) or a vacuum pencil (not shown) in the protected atmosphere of the inert-atmosphere glove box (256).

After the transfer of the TEM grid (131) with a TEM sample (280) attached to it to another TEM sample holder is completed, one or more new, empty TEM grids can be loaded into the TEM sample holder (130), and the whole process can be repeated.

Any other sensitive sample (such as a biological, toxic or oxygen-sensitive sample), which may require transfer in a controlled environment, can be transferred using the sample transfer system from the place where it was excised to the analytical instrument. For this transfer, other types of sample holder and other types of a transfer cassette can be used. The reader will see that transfer can also be performed under normal atmospheric pressure.

We claim:

1. An apparatus for the transfer of samples from an instrument, comprising:
   a capsule; the capsule further comprising:
   a door;
   the door having an opened and a closed position;
   a connecting flange for connecting to an instrument interface;
   the connecting flange aligned with the door;
   a sample transfer rod;
   the sample transfer rod moveable to selectively pass a sample through the door and out of the capsule, and to retract a sample through the door and into the capsule; and,
   a capsule door rod connected to the door for selectively opening and closing the door.

2. The apparatus of claim 1, further comprising:
   a sample-retraction switch;
   the sample-retraction switch closed by the movement of the sample transfer rod when a sample is retracted into the capsule.

3. The apparatus of claim 1, further comprising:
   a seal for sealing the door to the capsule;
   a door clamp; and,
   a door clamp rod connected to the door clamp, for clamping the door to the seal.

4. The apparatus of claim 1, where the door further comprises a flexible sheet.

5. The apparatus of claim 1, further comprising a sample holder removably connected to the sample transfer rod for transporting the sample.

6. An apparatus for the transfer of samples from an instrument, comprising:
   a capsule; the capsule further comprising:
   a gate valve system;
   the gate valve system further comprising:
   a door; the door comprising an opened and a closed position;
   a seal for sealing the door to the capsule;
   a door rod connected to the door for selectively opening and closing the door;
   a door clamp; and,
   a door clamp rod connected to the door clamp for clamping the door to the seal to form an air-tight environment within the capsule;
   a connecting flange for connecting to an instrument interface;
   the connecting flange aligned with the door;
   a sample transfer rod; and,
   the sample transfer rod moveable to selectively pass the sample through the door and out of the capsule, and to retract the sample through the door and into the capsule.

7. The apparatus of claim 6 further comprising:
   a sample-retraction switch;
   the sample-retraction switch closed by the movement of the sample transfer rod when the sample is retracted into the capsule.

8. The apparatus of claim 6, where the door further comprises a flexible sheet.

9. The apparatus of claim 6, further comprising a sample holder removably connected to the sample transfer rod.

10. An apparatus for the transfer of samples from an instrument, comprising:

a capsule; the capsule further comprising:
  a means for opening and closing the capsule;
    the means for opening and closing the capsule having an opened and a closed position;
  a connecting flange for connecting to an instrument interface;
    the connecting flange aligned with the means for opening and closing the capsule;
  a sample transfer rod;
  the sample transfer rod moveable to selectively pass a sample through the means for opening and closing the capsule, when open, and out of the capsule, and to retract a sample through the means for opening and closing the capsule, when open, and into the capsule.

11. An apparatus for the transfer of samples from an instrument, comprising:
  a capsule; the capsule further comprising:
  a gate valve system;
    the gate valve system further comprising:
      a door;
        the door comprising an opened and a closed position; the door further comprising a flexible sheet;
      a seal for sealing the door to the capsule;
      a door rod connected to the door for selectively opening and closing the door;
      a door clamp; and,
      a door clamp rod connected to the door clamp for clamping the door to the seal to form an air-tight environment within the capsule;
  a connecting flange for connecting to an instrument interface;
    the connecting flange connected to the capsule at the door;
  a sample transfer rod;
  a sample holder removably connected to the sample transfer rod;
  the sample transfer rod moveable to selectively pass the sample holder through the door and out of the capsule, and to retract the sample holder through the door and into the capsule;
  a capsule door rod for selectively opening and closing the door; and,
  a sample-retraction switch;
    the sample-retraction switch closed by the movement of the sample holder when the sample holder is retracted into the capsule.

12. A system for transferring samples from an instrument, the system comprising:
  an instrument interface; the instrument interface further comprising:
    a capsule purge system;
    an automated gate valve;
    a circuit for selectively opening and closing the automated gate valve;
    an interface flange for connecting the instrument interface to the instrument;
    a capsule-connecting flange for connecting a transfer capsule to the instrument interface; and,
  a transfer capsule; the transfer capsule further comprising:
    a door;
    a connecting flange for connecting to the instrument interface;
      the connecting flange aligned with the door.

13. The system of claim 12, where the transfer capsule further comprises:
  a sample transfer rod;
  the sample transfer rod moveable to selectively pass the sample through the door and outside the transfer capsule, and to retract the sample through the door and into the transfer capsule; and,
  a transfer capsule door rod for selectively opening and closing the door.

14. The system of claim 13, further comprising a sample holder removably connected to the sample transfer rod.

15. The system of claim 14, further comprising:
  a sample-retraction switch;
    the sample-retraction switch closed by the movement of the sample holder when the sample holder is retracted inside the transfer capsule.

16. The system of claim 15, where the circuit further comprises:
  a vacuum sensor connected to the instrument interface; the vacuum sensor having an output proportional to the pressure inside the instrument;
  a circuit connected to the vacuum sensor, the door clamp status switch and the sample-retraction switch; the circuit operational to cause the automated gate valve to open when:
    the sample-retraction switch is transitioned from closed to open,
    the door clamp status switch shows the door to be unlocked, and,
    the pressure inside the instrument is substantially at atmospheric pressure; and,
  the circuit further operational to cause the automated gate valve to close when the sample-retraction switch is closed and the pressure inside the instrument is at vacuum.

17. The system of claim 12, where the transfer capsule further comprises:
  a seal for sealing the door to the capsule;
  a door clamp; and,
  a door clamp rod connected to the door clamp, for clamping the door to the seal.

18. The system of claim 12 where the door of the transfer capsule further comprises a flexible sheet.

19. The system of claim 12, further comprising:
  a glove box;
    the glove box comprising a mating flange for removably connecting to the flange of the transfer capsule;
  a means for purging the glove box; and,
  a video camera connected to the glove box for observing its interior.

20. A method for transferring a sample from an instrument, comprising:
  providing an instrument interface to the instrument
  providing a sealable transfer capsule;
    the transfer capsule comprising a retractable sample holder;
  connecting the transfer capsule to the instrument interface;
  inserting the sample holder into the instrument;
  placing a sample on the sample holder inside the instrument;
  retracting the sample holder with sample into the transfer capsule; and,
  sealing the transfer capsule.

21. The method of claim 20 further comprising:
  sealing the instrument interface after retracting the sample holder with sample into the transfer capsule.

22. The method of claim 20 further comprising:
purging the transfer capsule with an inert gas after sealing the transfer capsule.

23. The method of claim 20 further comprising:
disconnecting the sealed transfer capsule from the interface;
connecting the sealed transfer capsule to a glove box;
unsealing the transfer capsule; and,
inserting the sample holder into the glove box.

24. The method of claim 23 further comprising:
purging the interior of the glove box with an inert gas prior to connecting the sealed transfer capsule to the glove box.

25. The method of claim 20 further comprising:
connecting the sealed transfer capsule to a second instrument while maintaining a vacuum in the sealed transfer capsule.

\* \* \* \* \*